United States Patent [19]

Ehrenfreund

[11] 4,310,694
[45] Jan. 12, 1982

[54] P-(ALKENYLAMINO) PHENYLAMINES

[75] Inventor: Josef Ehrenfreund, Allschwil, Switzerland

[73] Assignee: Ciba-Geigy Corporation, Ardsley, N.Y.

[21] Appl. No.: 224,982

[22] Filed: Jan. 14, 1981

Related U.S. Application Data

[62] Division of Ser. No. 128,610, Mar. 10, 1980, abandoned.

[30] Foreign Application Priority Data

Mar. 13, 1979 [CH] Switzerland .......................... 2379/79
Feb. 12, 1980 [CH] Switzerland .......................... 1134/80

[51] Int. Cl.³ .................... C07C 87/60; C07C 127/22; A01N 47/34
[52] U.S. Cl. ...................................... 564/442; 564/44; 424/322
[58] Field of Search ......................................... 564/442

[56] References Cited

U.S. PATENT DOCUMENTS 3,281,467 10/1966 Wilson et al. ..................... 564/442 X

FOREIGN PATENT DOCUMENTS 1936727 1/1970 Fed. Rep. of Germany ...... 564/442
2032135 9/1970 France ................................. 564/442

Primary Examiner—John Doll
Attorney, Agent, or Firm—Frederick H. Rabin

[57] ABSTRACT

Novel substituted N-(p-aminophenyl)-N'-benzoyl ureas of the formula

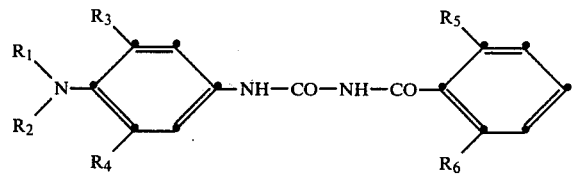

wherein each of $R_1$ and $R_2$ independently is $C_1$–$C_4$alkyl or $C_3$–$C_5$alkenyl, each of $R_3$ and $R_4$ independently is chlorine or bromine, and each of $R_5$ and $R_6$ independently is hydrogen, fluorine or chlorine, with the proviso that $R_5$ and $R_6$ are not both simultaneously hydrogen, processes for the manufacture of these compounds and compositions containing them for use in pest control, especially for controlling insects harmful to plants and animals. The novel compounds inhibit feeding damage and have in particular a pronounced ovolarvicidal and ovicidal action against plant-destructive insects.

1 Claim, No Drawings

P-(ALKENYLAMINO) PHENYLAMINES

This is a divisional of application Ser. No. 128,610 filed on Mar. 10, 1980 now abandoned.

The present invention relates to novel substituted N-(p-aminophenyl)-N'-benzoylureas, processes for their manufacture and their use in pest control.

The substituted N-(p-aminophenyl)-N'-benzoylureas of this invention have the formula I

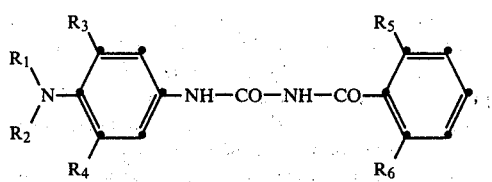

wherein each of $R_1$ and $R_2$ independently is $C_1$-$C_4$alkyl or $C_3$-$C_5$alkenyl, each of $R_3$ and $R_4$ independently is chlorine or bromine, and each of $R_5$ and $R_6$ independently is hydrogen, fluorine or chlorine, with the proviso that $R_5$ and $R_6$ are not both simultaneously hydrogen.

On account of their pesticidal action, preferred compounds of the formula I are those wherein $R_3$ and $R_4$ are chlorine. Those compounds of the formula I wherein $R_5$ and $R_6$ are fluorine are also of interest. Compounds of the formula I wherein at least one of $R_1$ and $R_2$ is allyl are also useful on account of their biological activity. Especially effective compounds of the formula I are those wherein one of $R_1$ and $R_2$ is allyl and the other is $C_1$-$C_4$alkyl.

The compounds of the formula I can be obtained by methods which are known per se (cf. inter alia, German Offenlegungsschriften Nos. 2 123 236 and 2 601 780).

Thus, for example, a compound of the formula I can be obtained by reaction of (a) a compound of the formula II

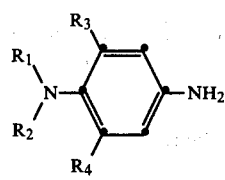

with a compound of the formula III

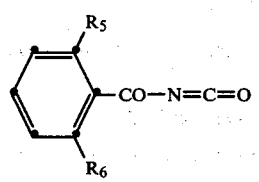

or (b) a compound of the formula IV

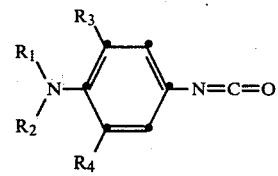

with a compound of the formula V

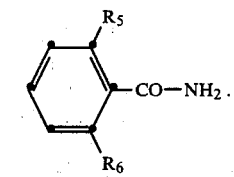

In the above formulae II, III, IV and V, the symbols $R_1$ to $R_6$ are as defined for formula I.

Processes (a) and (b) can preferably be carried out under normal pressure and in the presence of an organic solvent or diluent. Examples of suitable solvents or diluents are: ethers and ethereal compounds, such as diethyl ether, dipropyl ether, dibutyl ether, dioxane, dimethoxy ethane and tetrahydrofurane; N,N-dialkylated carboxamides; aliphatic, aromatic and halogenated hydrocarbons, especially benzene, toluene, xylene, chloroform, methylene chloride, carbon tetrachloride and chlorobenzene; nitriles, such as acetonitrile or propionitrile; dimethyl sulfoxide; and ketones, e.g. acetone, methyl ethyl ketone, methyl isopropyl ketone and methyl isobutyl ketone. Process (a) is normally carried out in the temperature range between $-10°$ and $100°$ C., preferably between $15°$ and $25°$ C., optionally in the presence of an organic base, e.g. triethylamine. Process (b) is carried out in the temperature range between $0°$ and $120°$ C., preferably at the boiling point of the solvent employed, and optionally in the presence of an organic base such as pyridine, and/or with the addition of an alkali metal or alkaline earth metal, preferably sodium.

The starting materials of the above formulae II, III, IV and V are known or, where new, can be prepared in accordance with known methods. Thus the p-phenylenediamines of the formula II can be obtained by N-alkylation or N-alkenylation of the corresponding p-nitro-anilines and subsequent reaction or catalytic hydrogenation of the nitro group to the amino group [cf. for example Rec. 21, 271 (1902); J. Am. Soc. 68, 1604 (1946); J. Org. Chem. 11, 378 (1946); Rec. 79, 995 (1970)]. The isocyanates of the formula IV can be obtained by reaction of the corresponding N,N-substituted p-phenylenediamines of the formula II with phosgene by methods commonly employed in the art. The compounds of the formula III can be obtained as follows (cf. J. Agr. Food Chem. 21 (3), 348-993, 1973):

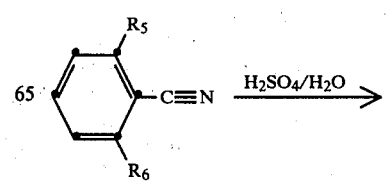

-continued

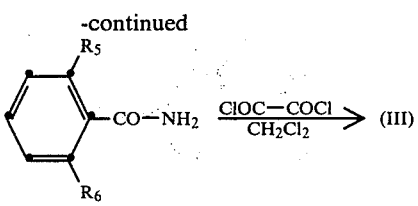

In the above formulae, $R_5$ and $R_6$ are as defined for formula I.

Those compounds of the formula II wherein at least one of $R_1$ or $R_2$ is a $C_3$-$C_5$alkenyl radical, are new and can be prepared by means of the methods referred to above. The novel starting compounds, which result in the valuable pesticides of the formula I, likewise constitute an object of the present invention.

It is already known that specific N-phenyl-N'-benzoylureas possess insecticidal properties (cf. German Offenlegungsschriften Nos. 2 123 236, 2 504 982, 2 537 413, 2 601 780 and 2 726 684; Belgian Pat. Nos. 832 304, 843 906, 844 066 and 867 046; and U.S. Pat. No. 4,089,975). Substituted N-phenyl-N'-2,6-dichlorobenzoylureas which are said to have insecticidal properties are known from J. Arg. Food Chem. 21, No. 3, 348 ff., (1973). On page 353 of this publication there are mentioned corresponding N-(4-dimethylamino)phenyl and N-(3-chloro-4-dimethylamino)phenyl derivatives which, however, have only insufficient insecticidal activity—as is evident from the Table III shown therein.

Surprisingly, it has been found that in contrast to the above compounds, the compounds of this invention have excellent pesticidal activity while being well tolerated by plants and having low mammalian toxicity. They are suitable in particular for controlling pests that attack plants and animals.

In particular, the compounds of the formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera.

In addition to their very advantageous action against flies, e.g. *Musca domestica,* and mosquito larvae, the compounds of the formula I are also suitable for controlling plant destructive feeding insects in ornamentals and crops of useful plants, especially in cotton (e.g. against *Spodoptera littoralis* and *Heliothis virescens*) and in vegetables (e.g. against *Leptinotarsa decemlineata* and *Pieris brassicae*). The ovicidal and ovolarvicidal action of the compounds of the formula I is to be singled out for special mention. When compounds of the formula I are ingested with the feed by adult insects, then a reduced egg laying and/or a reduced hatching rate is observed in many pests, especially in Coleoptera, e.g. *Anthonomus grandis.*

Furthermore, the compounds of the formula I are suitable for controlling ectoparasites in domestic animals and productive livestock, e.g. by treating animals, cowsheds, barns, stables etc., and pastures.

The action of the compounds of the formula I and the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates and chlorinated hydrocarbons.

Compounds of formula I are also combined with particular advantage with substances which exert a pesticidally potentiating effect. Examples of such compounds include: piperonyl butoxide, propynyl ethers, propynyl oximes, propynyl carbamates and propynyl phosphates, 2-(3,4-methylenedioxphenoxy)-3,6,9-trioxaundecane or S,S,S-tributylphosphorotrithioate.

The compounds of formula I may be used as pure active substance or together with suitable carriers and/or adjuvants. Suitable carriers and adjuvants can be solid or liquid and correspond to the substances conventionally used in the art of formulation, for example natural or regenerated substances, solvents, dispersants, wetting agents, thickeners, binders and/or fertilisers.

For application, the compounds of the formula I may be processed to dusts, emulsifiable concentrates, granules, dispersions, sprays, to solutions, or suspensions, in the conventional formulation which is commonly employed in application technology. In addition, cattle dips and spray races, in which aqueous preparations are used, may also be mentioned. These formulations are particularly suitable for controlling pests which are parasites of animals.

The compositions of the present invention are prepared in known manner by homogeneously mixing and/or grinding compounds of formula I with the suitable carriers, with or without the addition of dispersants or solvents which are inert to the active substances.

The compounds of formula I may be processed to the following formulations:

Solid formulations:

dusts, tracking powders and granules (coated granules, impregnated granules and homogeneous (granules).

Liquid formulations:

(a) water-dispersible active ingredient concentrates: wettable powders, pastes and emulsions;

(b) solutions.

The content of active ingredient in the above described compositions is between 0.1% and 95%.

The compounds (active ingredients) of formula I can, for example, be formulated as follows (throughout the present specification all parts and percentages are by weight):

DUST

The following substances are used to formulate (a) a 5% and (b) 2% dust:

(a)

5 parts of active ingredient,
95 parts of talc;

(b)

2 parts of active ingredient,
1 part of highly disperse silicic acid,
97 parts of talc.

The active ingredients are mixed and ground with the carriers.

GRANULES

The following substances are used to formulate 5% granules:
5.00 parts of active ingredient,
0.25 part of epoxidised vegetable oil,
0.25 part of cetyl polyglycol ether, 3.50 parts of polyethylene glycol,
91.00 parts of kaolin (particle size 0.3–0.8 mm).

The active ingredient is mixed with the epoxidised vegetable oil and the mixture is dissolved in 6 parts of acetone; the polyethylene glycol and cetyl polyglycol ether are then added. The resultant solution is sprayed on kaolin, and the acetone is subsequently evaporated in vacuo.

WETTABLE POWDERS

The following constituents are used to formulate (a) a 40%, (b) and (c) a 25%, and (d) a 10% wettable powder:

(a)

40 parts of active ingredient,
5 parts of sodium dibutylnaphthalenesulfonate,
54 parts of silicic acid;

(b)

25.0 parts of active ingredient,
4.5 parts of calcium ligninsulfonate,
1.9 parts of Champagne chalk/hydroxyethyl cellulose mixture (1:1),
1.5 parts of sodium dibutylnaphthalenesulfonate,
19.1 parts of silicic acid,
19.5 parts of Champagne chalk,
28.1 parts of kaolin;

(c)

25.0 parts of active ingredient,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselgur,
46.0 parts of kaolin;

(d)

10 parts of active ingredient,
3 parts of a mixture of the sodium salts of saturated fatty alcohol sulfates,
5 parts of naphthalenesulfonic acid/formaldehyde condensate,
82 parts of kaolin.

The active ingredients are homogeneously mixed with the additives in suitable mixers and the mixture is then ground in appropriate mills and rollers. Wettable powders are obtained which can be diluted with water to give suspensions of the desired concentration.

EMULSIFIABLE CONCENTRATES

The following substances are used to formulate (a) a 10%, (b) a 25% and (c) a 50% emulsifiable concentrate:

(a)

10.0 parts of active ingredient,
3.4 parts of epoxidised vegetable oil,
3.4 parts of a combination emulsifier consisting of fatty alcohol polyglycol ether and alkylarylsulfonate/calcium salt,
40.0 parts of dimethyl formamide,
43.2 parts of xylene;

(b)

25.0 parts of active ingredient,
2.5 parts of epoxidised vegetable oil,
10.0 parts of alkylarylsulfonate/fatty alcohol polyglycol ether mixture,
5.0 parts of dimethyl formamide,
57.5 parts of xylene;

(c)

50.0 parts of active ingredient,
4.2 parts of tributylphenol-polyglycol ether,
5.8 parts of calcium dodecylbenzenesulfonate,
20.0 parts of cyclohexanene,
20.0 parts of xylene.

By diluting these concentrates with water it is possible to obtain emulsions of the required concentration.

SPRAYS

The following ingredients are used to formulate (a) a 5% spray, and (b) a 95% spray:

(a)

5 parts of active ingredient,
1 part of epoxidised vegetable oil,
94 parts of ligroin (boiling range 160°–190° C.);

(b)

95 parts of active ingredient,
5 parts epoxidised vegetable oil.

The invention is further illustrated by the following Examples.

EXAMPLE 1

4.5 g (0.0175 mole) of 3,5-dichloro-4-N,N-diallylaminoaniline are dissolved in absolute ether. With cooling and exclusion of moisture, 3.5 g of 2,6-difluorobenzoylisocyanate are added to this solution. The precipitate formed after some time is filtered with suction and recrystallised from ethanol, affording $N^1$-[3,5-dichloro-4-N,N-diallylamino]phenyl-$N^2$-2,6-difluorobenzoylurea with a melting point of 150°–151.5° C.

The following compounds of the formula I are obtained in analogous manner:

| $R_1$ | $R_2$ | $R_3$ | $R_4$ | $R_5$ | $R_6$ | Melting point [°C.] |
|---|---|---|---|---|---|---|
| $CH_3$ | $CH_3$ | Cl | Cl | F | F | 209–211 |
| $CH_3$ | $CH_3$ | Cl | Cl | H | Cl | 189–190 |
| $CH_3$ | $CH_3$ | Cl | Cl | Cl | F | 194–196 |
| $CH_3$ | $CH_3$ | Cl | Cl | Cl | Cl | 209–211 |
| $CH_3$ | $CH_3$ | Cl | Cl | H | F | 203–204 |
| $CH_3$ | $CH_3$ | Br | Br | F | F | 215–219 |
| $CH_3$ | $CH_3$ | Br | Br | H | Cl | 208–210 |
| $CH_3$ | $CH_3$ | Br | Br | Cl | Cl | |
| $CH_3$ | $-CH_2-CH=CH_2$ | Cl | Cl | F | F | 146–148 |
| $CH_3$ | $-CH_2-CH=CH_2$ | Cl | Cl | Cl | Cl | 172–175 |
| $CH_3$ | $-CH_2-CH=CH_2$ | Cl | Cl | H | F | 128–131 |

-continued

| $R_1$ | $R_2$ | $R_3$ | $R_4$ | $R_5$ | $R_6$ | Melting point [°C.] |
|---|---|---|---|---|---|---|
| CH$_3$ | —CH$_2$—CH=CH$_2$ | Cl | Cl | F | Cl | 163-166 |
| CH$_3$ | —CH$_2$—CH=CH$_2$ | Cl | Cl | H | Cl | 114-117 |
| CH$_3$ | —CH$_2$—CH=CH$_2$ | Cl | Br | F | F | 156.5-159 |
| CH$_3$ | —CH$_2$—CH=CH$_2$ | Cl | Br | H | F | |
| CH$_3$ | —CH$_2$—CH=CH$_2$ | Br | Br | F | F | 170-172 |
| CH$_3$ | —CH$_2$—CH=CH$_2$ | Br | Br | Cl | Cl | |
| —CH$_2$—CH=CH$_2$ | —CH$_2$—CH=CH$_2$ | Cl | Cl | F | F | 150-151.5 |
| —CH$_2$—CH=CH$_2$ | —CH$_2$—CH=CH$_2$ | Cl | Cl | H | Cl | 148-150 |
| —CH$_2$—CH=CH$_2$ | —CH$_2$—CH=CH$_2$ | Cl | Cl | F | Cl | 171-173 |
| —CH$_2$—CH=CH$_2$ | —CH$_2$—CH=CH$_2$ | Cl | Cl | Cl | Cl | 166-168 |
| —CH$_2$—CH=CH$_2$ | —CH$_2$—CH=CH$_2$ | Cl | Cl | H | F | 104-106 |
| —CH$_2$—CH=CH$_2$ | —CH$_2$—CH=CH$_2$ | Br | Br | F | F | 148-152 |
| —CH$_2$—CH=CH$_2$ | —CH$_2$—CH=CH$_2$ | Br | Br | H | Cl | 128-130 |
| —CH$_2$—CH=CH$_2$ | —CH$_2$—CH=CH$_2$ | Br | Br | Cl | Cl | 174-176 |
| —CH$_2$—CH=CH$_2$ | —CH$_2$—CH=CH$_2$ | Br | Br | H | F | 117-119 |
| —CH$_2$—CH=CH$_2$ | -n-C$_3$H$_7$ | Cl | Cl | F | F | 132-134 |
| —CH$_2$—CH=CH$_2$ | -i-C$_3$H$_7$ | Cl | Cl | H | Cl | |
| —CH$_2$—CH=CH$_2$ | -n-C$_4$H$_9$ | Cl | Cl | F | F | 127-130 |
| —C$_2$H$_5$ | —CH$_3$ | Cl | Cl | H | F | |
| -n-C$_3$H$_7$ | -n-C$_3$H$_7$ | Cl | Cl | F | F | 136-137 |
| -n-C$_4$H$_9$ | —CH$_3$ | Cl | Br | H | Cl | |
| -n-C$_4$H$_9$ | -n-C$_4$H$_9$ | Cl | Cl | F | F | 159-161 |
| —(CH$_2$)$_3$—CH=CH$_2$ | —CH$_3$ | Cl | Cl | F | F | |
| -n-C$_4$H$_9$ | —CH$_3$ | Cl | Cl | F | F | 149-152 |

EXAMPLE 2

Action against *Musca domestica*

50 g of freshly prepared CSMA nutrient substrate for maggots were charged into beakers. A specific amount of a 1% acetonic solution of the respective active ingredient was pipetted onto the nutrient substrate present in the beakers. The substrate was then thoroughly mixed and the acetone subsequently allowed to evaporate over a period of at least 20 hours.

Then 25 one-day-old maggots of *Musca domestica* were put into each of the beakers containing the treated nutrient substrate for testing with each active ingredient at one of its given concentrations. After the maggots had pupated, the pupae were separated from the substrate by flushing them out with water and then deposited in containers closed with a perforated top.

Each batch of flushed out pupae was counted to determine the toxic effect of the active substance on the maggot development. A count was then made after 10 days of the number of flies which had hatched out of the pupae.

The compounds of Example 1 were very effective in this test.

EXAMPLE 3

Action against *Lucilia sericata*

1 ml of an aqueous formulation containing 0.5% of test substance was added at 50° C. to 9 ml of a culture medium. Then about 30 freshly hatched *Lucilia sericata* larvae were added to the culture medium, and the insecticidal action was determined after 48 and 96 hours by evaluating the mortality rate. In this test, compounds of Example 1 were very effective against *Lucilia sericata*.

EXAMPLE 4

Action against *Aedes aegypti*

Active ingredient concentrations of 10,5 and 1 ppm respectively were obtained by pipetting a specific amount of a 0.1% solution of the active ingredient in acetone onto the surface of 150 ml of water in each of a number of beakers. After the acetone had evaporated, 30 to 40 three-day-old larvae of *Aedes aegypti* were put into each of the beakers containing the active ingredient solution. Mortality counts were made after 1, 2 and 5 days respectively.

In this test, compounds of Example 1 were very effective against *Aedes aegypti*.

EXAMPLE 5

Insecticidal stomach poison action

Cotton plants were sprayed with a 0.05% aqueous emulsion of active ingredient (obtained from a 10% emulsifiable concentrate). After the spray coating had dried, the cotton plants were populated with *Spodoptera littoralis* and *Heliothis virescens* larvae in the L$_3$-stage. The test was carried out at 24° C. and 60% relative humidity.

In this test, the compounds of Example 1 exhibited a good insecticidal stomach poison action against Spodoptera and Heliothis larvae.

EXAMPLE 6

Action against *Spodoptera littoralis* and *Heliothis virescens* (larvae and eggs)

Three cotton plants having a height of about 15-20 cm and reared in pots were treated with a sprayable liquid preparation of the compound to be tested. After the spray coating had dried, the potted plants were placed in a metal container having a capacity of about 20 liters and covered with a glass plate. The humidity in the interior of the covered container was regulated such that no water of condensation formed. Direct light falling on the plants was avoided. The three plants were then infested altogether with:

(a) 50 larvae of *Spodoptera virescens* or *Heliothis virescens* in the L$_1$-stage;
(b) 20 larvae of Spodoptera larvae or *Heliothis virescens* in the L$_3$-stage;
(c) 3 egg deposits of *Spodoptera littoralis* or *Heliothis virescens*.

Two leaves of each plant were put into a plexiglass cylinder sealed at both ends with muslin. Two egg deposits of Spodoptera or a part of a cotton leaf with eggs of Heliothis deposited thereon were added to the leaves sealed in the cylinder.

Evaluation in comparison to untreated controls was made after 4 to 5 days, taking into account the following criteria:
(a) the number of still living larvae,
(b) inhibition of larval development and shedding,
(c) feeding damage (scoring and perforation damage),
(d) hatching rate (number of larvae hatched from the eggs).

In this test, the compounds of Example 1 exhibited good overall activity.

EXAMPLE 7

Ovicidal action against *Spodoptera littoralis*

Eggs of *Spodoptera littoralis* deposited on filter paper were cut out of the paper and immersed in a 0.05% by weight solution of the active ingredient in a 1:1 mixture of acetone-water. The treated deposits were then removed from this mixture and kept in plastic dishes at 21° C. and 60% humidity. The hatching rate, i.e. the number of larvae which had developed from the treated eggs, was determined after 3 to 4 days.

The compounds of Example 1 were very effective in this test.

EXAMPLE 8

Ovicidal action against *Epilachna varivestis*

A mixture was prepared from 20% by weight of active ingredient, 70% by weight of xylene and 10% by weight of a mixture of a reaction product of an alkyl phenol with ethylene oxide and calcium dodecylbenzenesulfonate. Aqueous emulsions containing 800 and 1600 ppm of active ingredient were prepared from this concentrate. 100 eggs of *Epilachna varivestis* (Mexican bean beetle), freshly deposited on leaves of *Phaseolus vulgaris*, were moistened with each of the above described aqueous emulsions (concentration: 800 and 1600 ppm respectively) and dried lightly. The treated egg deposits were kept in a ventilated container until the simultaneously deposited untreated controls had hatched.

The percentage kill was evaluated under a stereoscopic microscope.

The compounds of Example 1 were very effective in this test.

EXAMPLE 9

Ovicidal action against *Heliothis virescens* and *Leptinotarsa decemlineata*

Corresponding amounts of a wettable powder formulation containing 25% by weight of the compound to be tested were mixed with sufficient water to produce aqueous emulsions of increasing concentration. One-day-old egg deposits of Heliothis on cellophane and egg deposits of Leptinotarsa on potato leaves were immersed in these emulsions for 3 minutes and then collected by suction on round filters. The treated deposits were placed in petri dishes and kept in the dark. The hatching rate in comparison with untreated controls was determined after 6 to 8 days. Evaluation was made by determining the minimum concentration necessary for 100% kill of the eggs.

In this test the compounds of Example 1 exhibited very good ovicidal action against the tested pests.

EXAMPLE 10

Action against *Laspeyrasia pomonella* (eggs)

Egg deposits of *Laspeyrasia pomonella* not more than 24 hours old were immersed on filter paper for 1 minute in an acetonic solution containing 400 ppm of the compound to be tested.

After the solution had dried, the eggs were placed in petri dishes and kept at a temperature of 28° C. The percentage of larvae hatched from the treated eggs was evaluated after 6 days. The compounds of Example 1 were very effective in this test.

EXAMPLE 11

Chemosterilising action against *Anthonomous grandis*

Anthonomous grandis adults which were not more than 24 hours old after hatching were transferred in groups of 25 to barred cages. The cages were then immersed for 5 to 10 seconds in an acetonic solution containing 1.0% by weight of the active ingredient to be tested. After the beetles had dried, they were put into covered dishes containing feed and left for copulation and egg laying. Egg deposits were flushed out with running water twice to three times weekly, counted, disinfected by putting them for 2 to 3 hours into an aqueous disinfectant (e.g. "Acetamer B 100"), and then placed in dishes containing a suitable larval feed. A count was made after 7 days to determine whether larvae had developed from the eggs.

The duration of the chemosterilising action of the compounds to be tested was determined by monitoring the egg deposits over a period of about 4 weeks. Evaluation was made by assessing the reduction in the number of deposited eggs and hatched larvae in comparison with untreated controls.

The compounds of the formula I were very effective in this test.

What is claimed is:

1. A compound of the formula

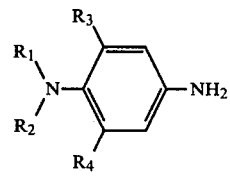

wherein
one of $R_1$ and $R_2$ is $C_3$–$C_5$ alkenyl, and the other of $R_1$ and $R_2$ is $C_3$–$C_5$ alkenyl or $C_1$–$C_4$ alkyl, and each of $R_3$ and $R_4$ is chlorine or bromine.

* * * * *